(12) United States Patent
McCune-Sanders et al.

(10) Patent No.: US 7,563,371 B2
(45) Date of Patent: Jul. 21, 2009

(54) TUBULAR ANAEROBIC DIGESTER

(76) Inventors: William Jason McCune-Sanders, 21 Cloarec Ct., #2, Burlington, VT (US) 05401; Theodore Guy Roberts, 1971 Huntington Rd., Richmond, VT (US) 05477

( * ) Notice: Subject to any disclaimer, the term of this patent is extended or adjusted under 35 U.S.C. 154(b) by 24 days.

(21) Appl. No.: 11/403,473

(22) Filed: Apr. 13, 2006

(65) Prior Publication Data

US 2006/0231488 A1 Oct. 19, 2006

Related U.S. Application Data

(60) Provisional application No. 60/670,982, filed on Apr. 13, 2005.

(51) Int. Cl.
*C02F 3/28* (2006.01)
*C02F 11/04* (2006.01)
*C12M 1/107* (2006.01)

(52) U.S. Cl. ............... 210/603; 435/293.1; 435/298.1; 435/300.1

(58) Field of Classification Search ............... 210/603, 210/615, 97, 116; 435/289.1, 293.1, 298.1, 435/300.1; 71/10
See application file for complete search history.

(56) References Cited

U.S. PATENT DOCUMENTS

| | | | | |
|---|---|---|---|---|
| 1,986,760 | A * | 1/1935 | Otto | 162/44 |
| 3,329,271 | A * | 7/1967 | Ward et al. | 210/150 |
| 3,981,803 | A * | 9/1976 | Coulthard | 210/178 |
| 4,192,849 | A | 3/1980 | Scheubeck et al. | |
| 4,252,901 | A * | 2/1981 | Fischer et al. | 435/167 |
| 4,284,508 | A | 8/1981 | Jewell | |
| 4,514,297 | A * | 4/1985 | Enqvist | 210/194 |
| H001337 | H * | 7/1994 | Hoeppel | 435/300.1 |
| 5,798,044 | A * | 8/1998 | Strohmeier et al. | 210/605 |
| 6,521,129 | B1 | 2/2003 | Stamper et al. | |
| 6,569,332 | B2 | 5/2003 | Ainsworth et al. | |
| 6,592,751 | B2 * | 7/2003 | Haridas | 210/97 |

(Continued)

FOREIGN PATENT DOCUMENTS

DE 19703142 * 7/1988

(Continued)

OTHER PUBLICATIONS

Marchaim, Uri, Biogas processes for sustainable development, 1992, vol. 95, Food and Agriculture Organization of the United Nations, Rome Italy.

(Continued)

*Primary Examiner*—Fred Prince

(57) ABSTRACT

A tubular plug flow digester system assembled from manufactured components, including a holding/heating tank (15) connected to a manifold (14) that feeds a single or multiple parallel injection pumps (12). These pumps force feedstock though check valves (13) and into single or parallel digester hulls. This hulls are composed of manufactured parts including tapered end sections (11) and hull sections (10) that can be assembled onsite to a configuration that accommodates operational needs. Biogas produced by this digester is pressurized due to a liquid column created by an elevated effluent outlet (25). Feedstock is inoculated with relevant microorganisms that promote the generation of methane-rich biogas. Inoculation members (26) positioned within the hulls shelter biofilms containing these microbes while allowing regions of the biofilm to slough or naturally release microbes into the flowing feedstock stream. Biogas is collected through a manifold (22) and its release is controlled by a regulator or a valve.

9 Claims, 4 Drawing Sheets

U.S. PATENT DOCUMENTS

| | | | |
|---|---|---|---|
| 6,645,374 B2 * | 11/2003 | Cote et al. | 210/151 |
| 6,673,243 B2 * | 1/2004 | Srinivasan et al. | 210/532.2 |
| 6,783,677 B1 * | 8/2004 | Irani | 210/603 |
| 6,860,997 B1 * | 3/2005 | Frederick et al. | 210/603 |
| 6,916,421 B1 * | 7/2005 | Cullinan et al. | 210/615 |
| 6,982,035 B1 | 1/2006 | O'Keefe | |

OTHER PUBLICATIONS

Miyamoto, Kazuhisa, Renewable biological systems for alternative sustainable energy production, 1997, vol. 128, Food and Agriculture Organization of the United Nations, Rome Itlaly.

Ljungdahl et al., Biochemistry and Physiology of Anaerobic Bacteria, 2003, Springer-Verlag New York, Inc., New York NY USA.

Ross et al., Handbook of Biogas Utilization, 2nd edition, Jul. 1996, U.S. Department of Energy, Southeastern Regional Biomass Program.

Koelsch et al., Anarobic Digesters for Dairy Farms, Agricultural and Biological Engineering Extension Bulletin 458, NY state college of ag. and life sciences, Ithaca, NY, Date Uknown.

Norddahl and Rohold, The Biorek Concept . . . , Bioscan Engineering A/S, May 2000, Tagtaekkervej 5, DK 5230 Odense, Denmark; email bno@bioscan.dk.

Wright, Overview of Anaerobic Digestion Systems for Dairy Farms, PRO-DAIRY Program, Biological and Environmental Engineering dept, Cornell University, Ithaca, NY, Mar. 2001.

Jewell et al., Evaluation of Anaerobic Digester Options for Groups of Dairy Farms in Upstate New York, USDA—NRCS Final Report, Jun. 1997, Cornell University, Ithaca, NY.

Lusk, Methane Recovery from Animal Manures the Current Opportunities Casebook, Sep. 1998, NREL, Golden, CO, available at www.doe.gov/bridge/home.html.

Valentine et al., High Rate Anaerobic Fixed-Film Reactor for the Food Processing Industry, Final Report on GRTI project A-4817, Jul. 1998, Georgia Institute of Technology.

Martin, A Comparison of Dairy Cattle Manure Mgmt. w & w/o Anaerobic Digestion and Biogas Utilization, Mar. 2003, AgSTAR Program, US EPA, Washington, DC.

Burke, Dairy Waste Anaerobic Digestion Handbook, Jun. 2001, Environment Energy Company, Olympia, WA.

Miyamoto, Kazuhisa, Renewable biological systems for alternative sustainable energy production, 1997, vol. 128, Food and Agriculture Organization of the United Nations, Rome Italy.

* cited by examiner

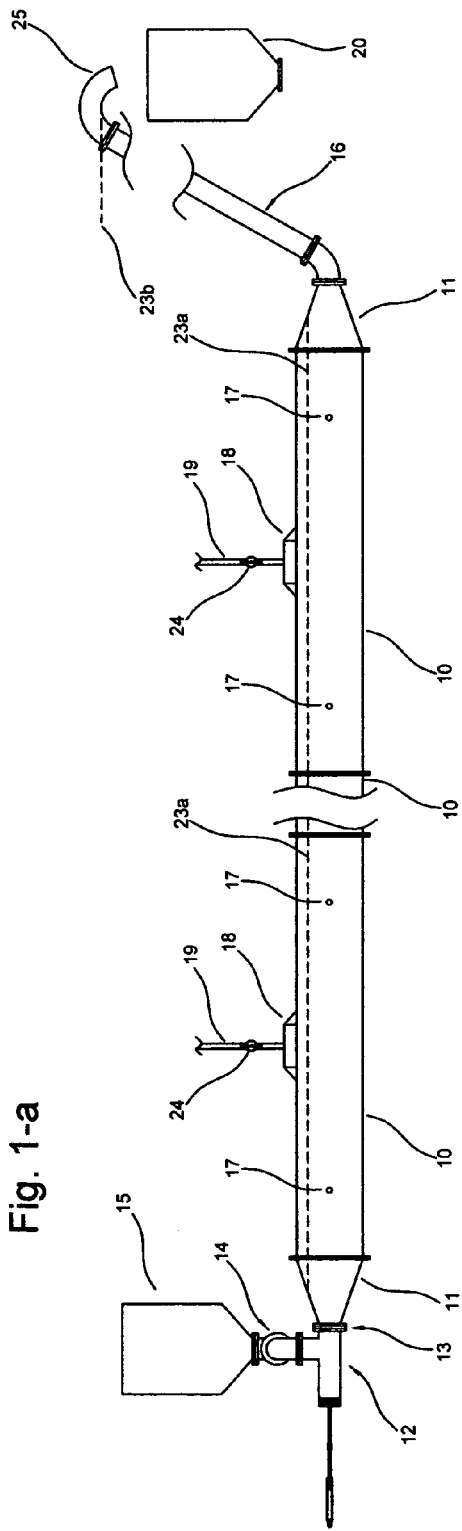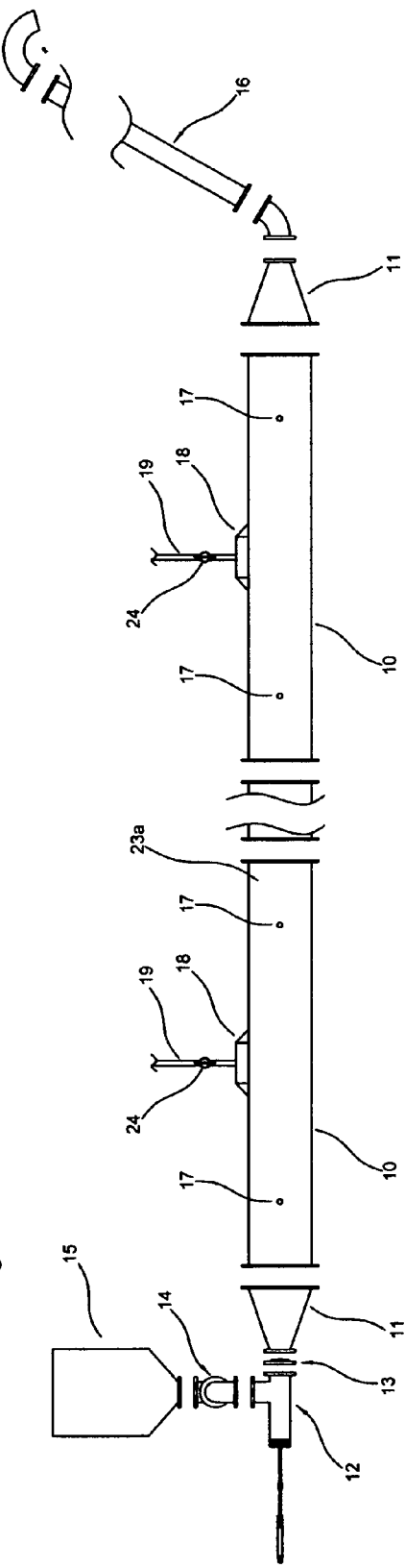
Fig. 1-a
Fig. 1-b

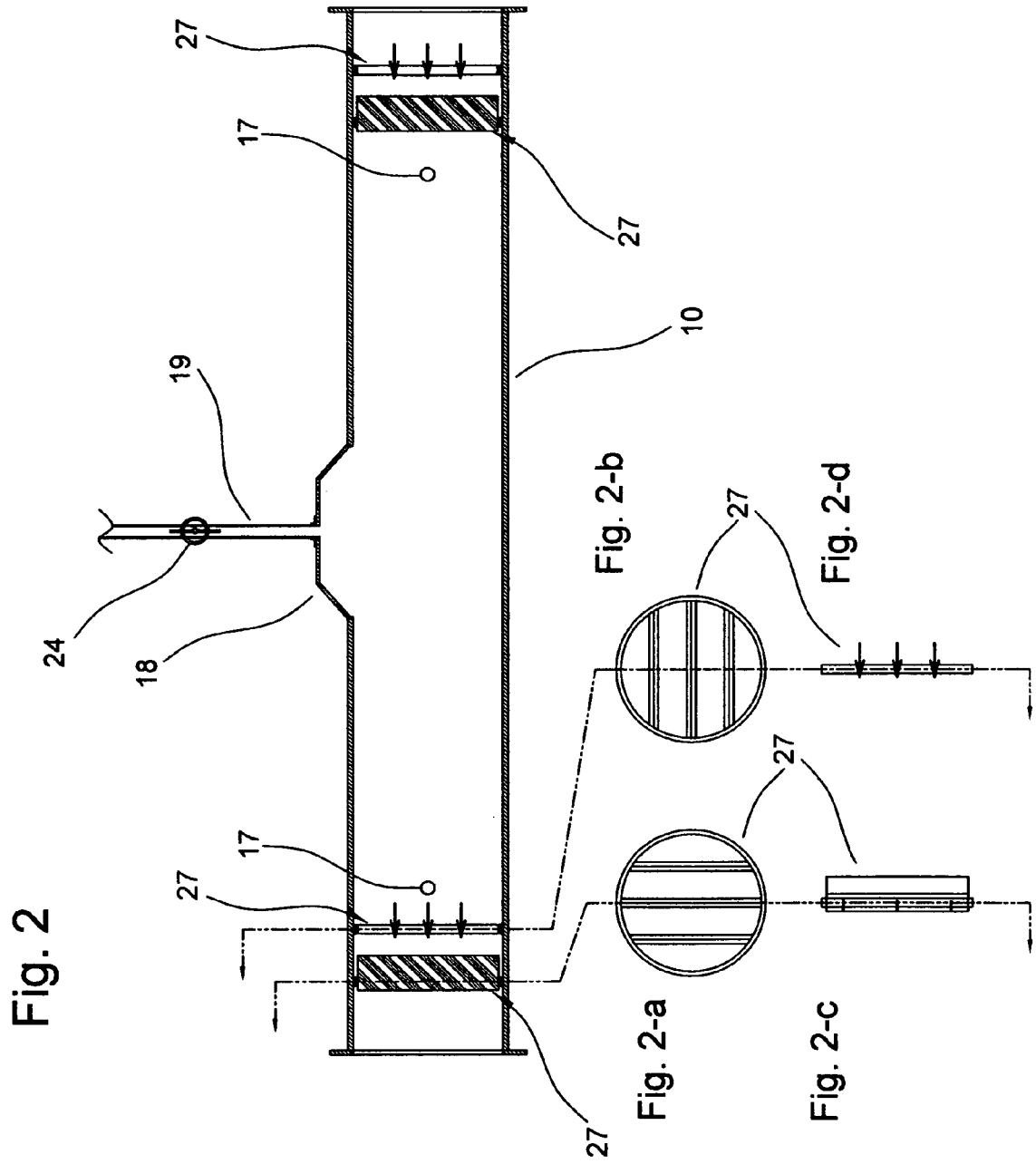

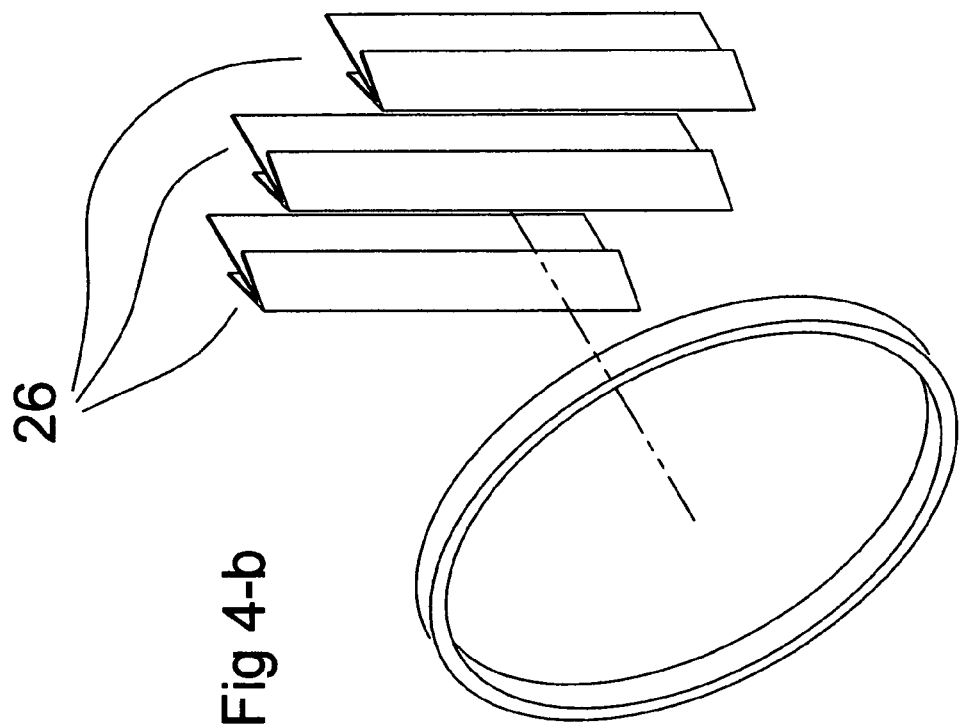
Fig 4-b
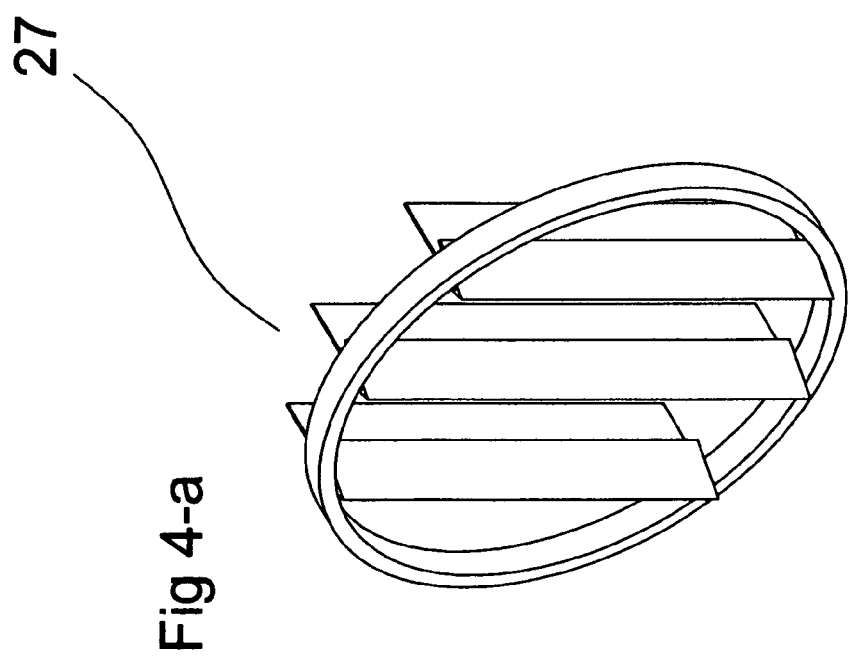
Fig 4-a

TUBULAR ANAEROBIC DIGESTER

CROSS-REFERENCE TO RELATED APPLICATIONS

This applications claims the benefit of PPA Ser. No. 60/670,982, filed Apr. 13, 2005 by the present inventors.

FEDERALLY SPONSORED RESEARCH

This project was partially funded through a grant from the USDA. In accordance with the solicitation number USDA-GRANTS-031803-001:
A. Allocation of rights to patents, inventions and copyrights shall be in accordance with 7 CFR 3019.36. This regulation provides that small businesses normally may retain the principle worldwide patent rights to any invention developed with USDA support. This provision also applies to commercial organization for the purposes of this grant.
B. Rule 37 CFR Part 401.14 requires the disclosure of each subject invention to the Federal Agency within two months after the inventor discloses it in writing to contractor personnel responsible for patent matters. Invention disclosure statements pursuant to 37CFR Part 401.14(c) shall be made in writing to:
Management Services Division
Grants and Agreements Staff
1400 Independence Avenue, SW
Room 5221 South Building
Washington, DC 20250
C. USDA receives a royalty-free license for Federal Government use, reserves the right to require the patentee to license others in certain circumstances, and requires that anyone exclusively licensed to sell the invention in the United States must normally manufacture it domestically.

BACKGROUND OF THE INVENTION

1. Field of the Invention

This invention relates to the use of anaerobic digesters to generate fuel from biomass through biological processes.

2. Prior Art

Animal manures, spoiled animal feed, food wastes and other forms of biomass can be used for producing a biogas rich in methane. This biogas can be produced using anaerobic digesters and is useful as a fuel for generators and other applications. Anaerobic digesters can be made according to a multitude of different architectures that are typically tailored to the needs of a specific user.

From the 1930s onwards digesters have been built through national programs in India, China and other Southeast Asian countries to supply cooking fuels for small family farms. More recently, developing countries have developed a strong interest in using digester technology to address the need for inexpensive fuels for heating and electrical generation. Farms in the Europe and North America have recognized that digesters offer an attractive way of processing animal wastes to reduce associated odors and/or fuel generators.

Over the past several decades, this technology has proven itself feasible on large farm operations (LFOs) and has repeatedly failed on small and medium-sized farms. This is due, in large part, to the expense of building large structures to hold the feedstock (generally manure) for the length of time required for biological processes to produce biogas. Regardless of the increasing variety of available architectures, most of these designs incorporate disadvantages that hinder their use on small and mid-sized farms:

(a) Most digesters are designed to be economical only at a large scale. Their construction requires the employment of engineers to resize and adapt the specific design to any particular construction site. Specialty contractors are generally required to build the digester due to design requirements for poured and reinforced concrete and other heavy equipment and/or materials specified in these designs.

(b) Their operation and maintenance requires more time and expense than small or mid-sized farmers can afford. Most digesters lack specific mechanisms that simplify the periodic removal of sediments that will naturally accumulate within the digester.

(c) Most digesters require a large array of pumps and other electrical and mechanical devices that must run continuously for effective operation. The inevitable failure of these devices in the farm's harsh environment may greatly inconvenience farmers whose operations already call for heavy maintenance schedules. Moreover, these devices may use a significant fraction of the energy value of the biogas, making digesters feasible only on large-scale farms.

(d) Most plug flow designs appropriate for manures have flexible membrane covers that have a limited lifetime and failure prone systems for attachment, leading to biogas leaks. The cover must be removed to allow periodic cleanouts, and the difficulty of this process leaves the owner/operator balancing this cost against the potential decrease in performance due to accumulated sediments.

(e) Most digesters are designed to store a useful amount of biogas within the digester itself. Most digesters, however, store this biogas at low pressure that may require that gas piping be of larger diameter or that gas use be restricted to within a short distance of the digester. Digesters that are mechanically pressurized typically require the use of compressors, pumps or compressed gases. Additionally, the pressurized digester itself becomes a pressure vessel that requires elaborate valving to enable feedstock flow.

(f) Most digesters that handle high levels of solids fall into the low range of efficiency with regard to their ability to convert volatile solids in the feedstock to methane. Digesters of the 'plug flow' variety may be vulnerable to low efficiency operation, due to continuous loss of microbes that dwell in the feedstock. High efficiency digesters typically employ a 'fixed-film' that supports development of a microbial biofilm, where digestion of feedstock is thought to occur as nutrients in the feedstock permeate this biofilm. These fixed-film digesters, however, require that the feedstock contain less than 8% solids, in order to avoid destroying the biofilm. This upfront removal of solids causes a significant part of the odor-causing and digestible material to be excluded from receiving the benefits of anaerobic digestion.

(g) Farmers may have to finance the purchase of even a small-scale digester. Lending institutions may be less likely to give loans for fixed assets. Most digesters, being essentially custom-built using poured concrete and permanent structures must be considered to be fixed assets.

BACKGROUND OF THE INVENTION—OBJECTS AND ADVANTAGES

In consideration of the limits to the application of existing patents for small and medium-sized farms and other small-scale opportunities to produce biogas from biomass, several objects and advantages of the present patent are:

(a) to provide a digester that achieves an economy of scale through mass-production and shipment to the purchasing farm;

(b) to provide a digester that can be assembled without the placement of permanent structures without the need for custom engineering and/or construction companies.

(c) to provide a digester which is simple and cost-effective to operate, requiring that mechanical components need run only periodically or part-time;

(d) to provide a digester that can be easily cleared of accumulated sediments in a short period of time and with little human resource;

(e) to provide a digester that is self-pressurizing and in which pressure is passively maintained in an open vessel that supports a continuous flow of feedstocks;

(f) to provide a digester that can accept feedstocks with greater than 8% and less than 18% solids and operate with efficiencies of greater than is typical for plug flow digesters;

(g) to provide a digester that can be disassembled and relocated and therefore be classified as a moveable asset;

Further objects and advantages are to provide a digester that can be built from long or short tubular subsections, according to the format that is most easily produced and shipped to the customer, that can be assembled from these subsections into a single digester, or into multiple, parallel digesters to meet the needs and practices of a farm or biomass producer, that has removable ends that allow simple cleanout, that can self-inoculate the feedstock with relevant organisms through the continuous abrasion of biofilms growing on specifically-shaped surfaces that are placed at intervals in the flow of the feedstock, and that takes advantage of as many passive apparatus as possible to provide energy efficient operation. Still further objects and advantages will become apparent from a consideration of the ensuing description and drawings.

SUMMARY

In accordance with the present invention our tubular anaerobic digester comprises a tubular digester hull assembled from pre-made sections, that contains a large bubble of biogas over the biomass feedstock, where the feedstock is pushed into the digester using a pump and baffles, and where the biogas is drawn off of the digester through a pressure regulated gas manifold, and a set of inoculation surfaces are placed at intervals along the length of the digester, and where the digested feedstock is forced up a final inclined section that provides a water column to passively pressurize the biogas contained within the digester.

DRAWINGS—FIGURES

FIGS. 1a and 1b shows an exploded view of the same embodiment of a single tubular digester hull FIGS. 2 to 2d show a side and section views of a single section of a tubular anaerobic digester hull with section views showing the placement of inoculation members in an array.

FIGS. 4a and 4b shows an isometric view of a preferred embodiment of an array of inoculation members.

DRAWINGS—REFERENCE NUMERALS

Figure 3:
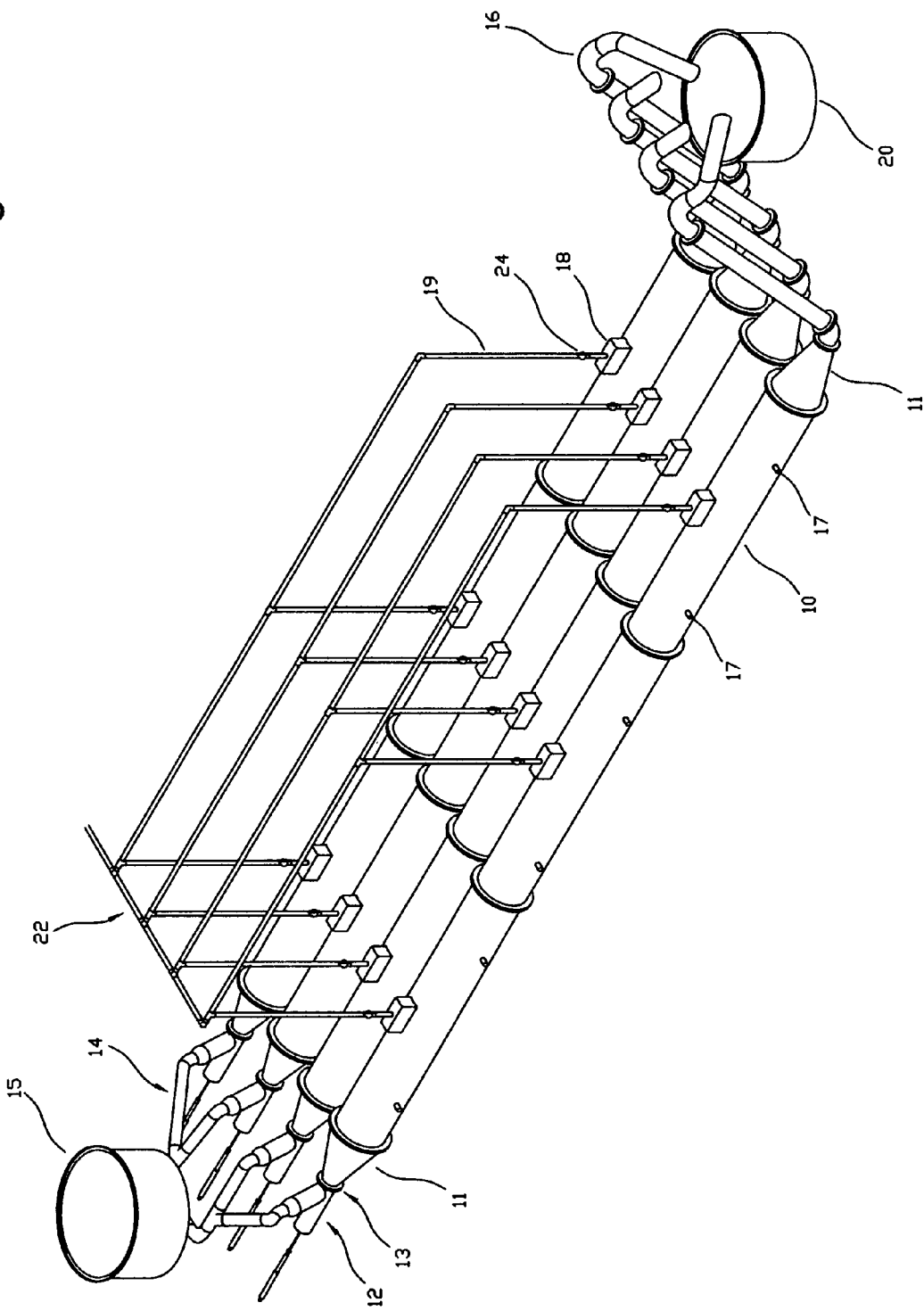
FIG. 3 shows a view of a preferred embodiment of a multi-hull anaerobic digester.

| | |
|---|---|
| 10 | tubular hull section |
| 11 | tapered end section |
| 12 | injector pump |
| 13 | digester check valve |
| 14 | feedstock manifold |
| 15 | holding/heating tank |
| 16 | elevated outlet section |
| 17 | sampling ports |
| 18 | gas riser |
| 19 | gas mast |
| 20 | effluent feedstock tank |
| 22 | gas manifold |
| 23a | biogas/feedstock interface |
| 23b | outlet level |
| 24 | gas shut-off valve |
| 25 | effluent outlet |
| 26 | inoculation member |
| 27 | inoculation member array |

DETAILED DESCRIPTION—FIGS. 1-4—PREFERRED EMBODIMENT

A preferred embodiment of the tubular anaerobic digester of the present invention is illustrated in FIG. 1a (side view) and FIG. 2a (exploded view). The digester hull is assembled from tubular hull sections (10) connected in series. An assembly of such hull sections is connected front and rear to tapered ends (11) that allow the digester hull to entrap gas above the level of the feedstock/gas interface (23a). In the preferred embodiment the tubular sections are constructed from a corrosion resistant material that can be custom formed, such as high density polyethylene or fiberglass. The cross-section of the hull is shown to be circular, however, other shapes, such as trapezoidal, ovoid, triangular and rectangular each exhibit relative advantages in structure and process.

The overall digester hull dimensions are scaled to provide a range of a 10 to 30 day feedstock retention time. The ratio of the wetted cross sectional area of the hull to the digester hull length should generally be not more than 1 to 3. The lower limit of this ratio is defined by the practicality of the feedstock flow, materials investment and available space. Hull sections can be sized for ease of manufacturing, transportation and assembly. In the preferred embodiment the hull sections have flanged ends that are configured for gas tight assembly and potential disassembly and re-use.

An injector pump (12) is installed at the influent end of the digester. In the preferred embodiment, this injector pump is hydraulically driven. A check-valve (13) is installed between the housing of the injector pump and the tapered end of the digester hull. A feedstock manifold (14) directs feedstock material into the injector pump from a holding/heating tank (15). The feedstock manifold can be made of a heavy plastic material such as poly vinyl chloride (PVC) and may where possible be constructed using standardized components, such as schedule 40 PVC pipe and fittings or other durable materials. In the preferred embodiment the heating/holding tank (15) is sized to hold the manure for between $\frac{1}{8}^{th}$ to one volume of the feedstock added per day in order to minimize the size of this tank.

In the preferred embodiment a gas riser (18) is located at some point along the top surface of each hull section. A gas mast (19) is attached to this riser. A gas tight shutoff valve (24) may be installed in the gas mast. The riser provides additional clearance between the level of the feedstock and the base of the gas mast to help prevent clogging. A ball float valve (not shown) may be installed at the base of the gas mast to help prevent fouling of the gas mast with feedstock. The gas mast connects to horizontal sections of gas pipe to form the gas manifold (22) that allows the gas to be collected from all sections of the digester hull and from multiple parallel hulls shown in FIG. 3.

At the effluent end of the digester hull an elevated outlet section, inclined or vertical (16) is attached to both trap the gas within the digester and provide an elevated liquid column. The elevated outlet (25) is open to the atmosphere and establishes the height of the liquid column that pressurizes the digester contents. A regulator or valve is placed at the outlet of the gas manifold (not shown) to control the release of the biogas while maintaining pressure. Effective regulation of this pressure will maintain the level of feedstock/biogas interface (23a). The difference in height of the feedstock/biogas interface and the outlet level (23b) determines the internal pressure of the digester's contents and, in particular, the maximum line pressure for the biogas.

The digester outlet is positioned over an outlet tank (20) of a size determined by the subsequent processing. On a typical dairy farm, the digester effluent may simply be returned to the manure storage pit.

FIG. 2 shows a sectional view of a hull section with isometric views of the inoculation member array in place within the hull. Members (26) individually or in arrays (27) may be placed multiply or singly within each hull section or may be placed in only a subset of these locations, depending on the nature and flow of the feedstock. FIGS. 2a to 2d show orthographic front and side views of the inoculating member arrays as placed in this preferred embodiment. The members as shown are positioned to allow passage of objects that may enter the feedstock stream, while still providing exposure of the feedstock to inoculating surfaces.

The members are designed with sheltered regions to foster continuous growth of biofilm, with more exposed regions where biofilms will be subject to the abrasive action of the flowing feedstock. In the preferred embodiment, the movement of the feedstock is periodic, rather than continuous, allowing biofilms to regenerate within these exposed regions.

Our interest in supporting this biofilm is to maintain a population of microbes that continually slough off the grating and colonize the fibers in the manure. Use of an inoculation grating is a significantly different approach to microbial management as compared to "fixed-film" digesters that utilize biofilms as the primary surface on which biological activities are supported. Most fixed-film digesters accept only low percentages of solids in their feedstocks, and are reliant on the support surfaces to maintain microbial populations. Our digester differs from these in that we utilize a significantly smaller fixed surface that through sloughing and abrasion by the moving feedstock releases the microbes throughout the manure as it moves by the grating. The feedstocks used in our tubular plug-flow digesters are rich in fibers that support microbial growth, so only brief exposure to our inoculation members is necessary to support biological activity, as opposed to "fixed-film" digesters where the feedstock is expected to be continually exposed to biofilm-coated fixed surfaces.

FIG. 3 shows a preferred embodiment in which four digester hulls are arranged in parallel. A manifold (14) connects the heat/holding tank (15) to an injection pump (12) at the influent end of each digester hull. In the preferred embodiment a check valve (not shown) is installed between the manifold junction at each injector pump. An alternative embodiment is to integrate the check valves within the piston of the injector pump.

The effluent outlets shown in FIG. 3 are separated from one another. An alternative configuration is to join the effluent ends at the level of the digester hulls and provide a single elevated section that can be inclined or vertical.

DETAILED DESCRIPTION—FIGS. 1-4—OPERATION

As with virtually all forms of digesters, processing of the feedstock must generally take place to adjust the moisture content, to add heat, and to screen out large items that may jam the digester's internal workings. These processing steps are subject to the needs of each farm or biomass source and so are not discussed here, though some provision for such processing must be built into digester systems of any scale or architecture.

The tubular digester presented herein accepts feedstocks of approximately 80-90% moisture content, be heated to at least 85° F. and have had most long fibrous material, such as straw, hay or bale strings removed or reduced to less than 3 inches in length.

The basic principle of our tubular digester is that with each addition of feedstock by the injector pump (12), there is displacement of digested feedstock from the effluent outlet (25). The feedstock material is either processed within or carried to a feedstock tank (15)) that is positioned over the injection pumps (12) to allow gravity-assisted movement of feedstock through the feedstock manifold (14) into the injection pump cylinder. A check valve positioned before each injector pump enables feedstock to flow into the pump cylinder, nullifying the effects of back-pressure and suction as the piston reciprocates. The injection pistons forces feedstock through a check valve (13) positioned between the injection pump and the tapered end of the digester (11) to prevent backflow into and stalling of the injection pumps.

As feedstock flows into and through the digester, it passes through a number of inoculation member arrays (27). These members are placed perpendicular to the flow of feedstock through the digester in such a way that it becomes colonized by microbes that promote the production of methane. As is now generally understood, these organisms naturally form a colonial layer on fixed surfaces, called a biofilm. As organisms are abraded from this biofilm, they are exposed to and may colonize the particulate surfaces of the feedstock. From these colonies the organism may spread within the feedstock and more effectively process the feedstock to produce methane as compared to typical plug flow digesters that have no specific provision for such inoculation.

After passing through the inoculation grating, the manure moves through the digester hull (10) with a retention time of between 10 and 30 days. The digester hull is constructed from several similar sections (FIGS. 1 and 3) with inoculation member arrays positioned typically at the front of each hull section. The use of multiple inoculation member arrays benefits digester operation by providing stable habitats for a variety of microorganisms in what may become different metabolic zones of the digester. As the methane-containing biogas is produced, it rises to the top of the digester hull and collects as a bubble that may occupy up to ⅓ of the volume of the tube. This volume is determined by the position of the inlet and outlet ports in the tapered hull sections. As shown in FIGS. 1 to 4 these tapered sections are axially symmetric, however, alternatively asymmetric tapered sections may be used to provide additional space for gas storage. Yet another alternative would be to place baffles across the top of the digester hull at each end to create a space that will trap gas (not shown). Biogas can be withdrawn from the digester through the gas masts (19) and/or the gas manifold (22).

By elevating the digester's outlet we have created two advantages. First, the digester effluent is expelled at a height that often precludes the need for a pump to move effluent materials towards the next step of effluent feedstock processing. Second, the height between the outlet level and the surface of the slurry in the digester represents a water column that exerts pressure on the contents of the digester hull. The level that the outlet is positioned can produce internal pressures of up to 15 psi. More typically the outlet is positioned to provide biogas at a pressure of about 5 psi. This provides sufficient pressure to drive gas through gas conditioning filters and to ultimately be used as fuel for generator sets, boilers, adsorption chillers or other compatible applications. Again, as fresh feedstock is injected into the digester, effluent feedstock is displaced from the effluent end. This effluent slurry has substantially reduced odor and reduced fecal coliform counts, but is enriched for the reduced forms of nitrogen; ammonia and ammonium. This effluent should be further treated by any of several means to prevent the off-gasing of ammonia and the continued production of methane.

The contents of the digester hull must be heated to between 30°-40° C. (85°-105° F.) to sustain a population of mesophilic organisms. In the preferred embodiment this is done by coiling hydronic heat tubing around the outside of the hull in wraps spaced 4 to 24 inches from one another (not shown). A thermostat would be positioned within the digester hull to measure the actual temperature of the digesting feedstock. The hull should be insulated from ambient temperatures and should be isolated from groundwater (not shown). A skilled practitioner of the arts will discover numerous ways to provide such insulation. If the digester is held at mesophilic temperatures, the conversion efficiency of volatile solids to biogas should be approximately 40%, which is typical for plug flow digesters.

Materials for construction of the hull must be impermeable to methane gas and should be resistant to acidic conditions, organic solvents, abrasion by sand and grit, and corrosion by hydrogen sulfide. Plastics, such as high density polyethylene and fiberglass are ideally suited to this application, being gas tight and highly abrasion- and chemical-resistant. Pre-cast concrete may also serve this purpose, although some kind of coating should be applied to the inner surfaces to increase the useful lifetime of any concrete exposed to the digester interior. Concrete, because of its weight and fragility, would require careful handing during disassembly while cleaning. Stainless steel is another suitable material with respect to its physical properties, however the cost of materials would, at this time, be prohibitively expensive. There may be other types of materials that would be suitable, in particular layered materials that provide insulative qualities to the digester hull. Sample ports (17) may be positioned along the lengths of the digester to allow sampling of the feedstock at different stages of digestion. The rate of feeding and retention time should be determined periodically by measuring the residual levels of volatile solids (VS) and volatile organic acids (VOAs). Material near the end of the digester should show a reduction in volatile solids of at least 30% and should contain minimal levels of VOAs. These conditions indicate that both the acid forming organisms and the methanogens are present in adequate numbers and actively metabolizing.

As mentioned above, each time feedstock is injected into the digester an equal volume of effluent feedstock is displaced from the effluent end of the digester. This material may be collected and is generally either stored for use as a fertilizer, or may be separated into solids and liquids to derive additional benefits from the digester effluent.

CONCLUSION

Accordingly, the reader will see that the tubular anaerobic digester of this invention can be used to derive biogas from a biomass feedstock of relatively high solids content, as found on small and mid-sized farms that use a scrape system for manure management. The tubular digester described herein has the additional advantages in that it permits the mass production and shipping of an anaerobic digester;

it permits the assembly of a digester without the need for engineering or heavy construction specialists;

it permits the direct use of feedstock slurries with high solids contents;

it allows the digester to operate with a high degree of energy efficiency;

it permits the disassembly of the digester for resale, liquidation, or reconfiguration;

it permits a variety of digester configurations that can be tailored to a range of operation sizes, needs and conditions.

Although the description above contains many specificities, these should not be construed as limiting the scope of the invention, but merely providing illustrations of some of the presently preferred embodiments of this invention.

Thus the scope of the invention should be determined by the appended claims and their legal equivalents, rather than the examples given.

The invention claimed is:

1. An anaerobic digester apparatus, comprising:
   a. a hull assembly of at least one tubular section;
   b. tapered tubular sections at each end of said hull assembly, forming one inlet opening and one outlet opening;
   c. an injection pump to move feedstock into said inlet opening of said hull assembly;
   d. a valve located between said injection pump and said inlet opening to prevent said feedstock from flowing back through said inlet opening;
   e. at least one gas outlet located along the top of said hull assembly that permits the withdrawal of biogas from said hull assembly;
   f. a regulator for controlling the release pressure of said biogas in said hull assembly;
   g. an open-ended upwardly inclined pipe connected to said outlet end of said hull assembly, creating a column of said feedstock that pressurizes the contents of said hull assembly, the outlet height of said inclined pipe determining the degree of pressurization of said biogas entrapped in said hull assembly;

whereby said feedstock can be biologically acted upon to produce biogas.

2. The apparatus of claim 1, wherein the cross-sectional shape of said hull assembly is circular.

3. The apparatus of claim 1, wherein said tapered tubular sections are conical in shape.

4. The apparatus of claim 1, wherein the withdrawn biogas is stored for later use.

5. The apparatus of claim 1, wherein said gas outlets are linked together by a manifold outside of said hull assembly.

6. An anaerobic digester apparatus, comprising:
   a. multiple hull assemblies arranged in parallel, each hull assembly comprised of at least one tubular section;

b. tapered tubular sections, forming one inlet opening and one outlet opening at each end of each individual hull assembly;
c. an infeed manifold to distribute feedstock to the inlet opening of each individual hull assembly;
d. at least one injection pump to move said feedstock into each individual hull assembly;
e. at least one valve to prevent said feedstock from flowing back through said inlet opening;
f. at least one gas outlet connected to each individual hull assembly that permits the withdrawal of biogas from each individual hull assembly;
g. at least one regulator connected to each individual hull assembly for controlling the release pressure of said biogas from each individual hull assembly;
h. at least one gas manifold outside of the hull assemblies that links together the multiple gas outlets;
i. an open-ended upwardly inclined pipe connected to said outlet end of each individual hull assembly, creating a column of said feedstock that pressurizes the contents of each individual hull assembly, the outlet height of said inclined pipe determining the degree of pressurization of said biogas entrapped in each individual hull assembly;

whereby the quantity and size of said hull assemblies can be scaled to meet different volumetric needs.

7. The apparatus of claim 6, wherein the cross-sectional shape of said hull assembly is circular.

8. The apparatus of claim 6, wherein said tapered tubular sections are conical in shape.

9. The apparatus of claim 6, wherein the withdrawn biogas is stored for later use.

* * * * *